United States Patent [19]
Sinnett et al.

[11] Patent Number: 5,773,649
[45] Date of Patent: Jun. 30, 1998

[54] DNA MARKERS TO DETECT CANCER CELLS EXPRESSING A MUTATOR PHENOTYPE AND METHOD OF DIAGNOSIS OF CANCER CELLS

[75] Inventors: Daniel Sinnett, Boucherville; Damian LaBuda, Montéal; Maja Krajinovic, Montéal; Chantal Richer, Montré, all of Canada

[73] Assignee: Centre de recherche de l'Hôpital Sainte-Justine, Montréal, Canada

[21] Appl. No.: 661,168

[22] Filed: Jun. 10, 1996

[51] Int. Cl.[6] ..................................................... C12P 19/34
[52] U.S. Cl. ........................................ 435/91.2; 536/24.3
[58] Field of Search ............................ 435/6, 91.1, 91.2; 536/24.3

[56] References Cited

PUBLICATIONS

Speicher, M.R., 1995, *Oncology Res.*, 7:267–275.
Kolodner, R.D. et al., 1995, *TIBS*, 20:397–401.
Sinnett, D. et al., *Genomics*, 7:331–334.
Zietkiewicz, E. et al., 1992, *Proc. Natl. Acad. Sci. USA*, 89:8448–8451.
Peinado, M.A. et al., 1992, *Proc. Natl. Acad. Sci. USA*, 89:10065–10069.

*Primary Examiner*—W. Gary Jones
*Assistant Examiner*—Amy Atzel
*Attorney, Agent, or Firm*—Swabey Ogilvy Renault; France Côté

[57] ABSTRACT

The present invention relates to a method of diagnosis or prognosis of tumor cells in a patient displaying a mutator phenotype in the tumor which comprises the steps of: a) obtaining a genomic DNA sample of the tumor; b) obtaining a genomic DNA sample of a tumor-free tissue of the patient; subjecting the DNA samples of steps a) and b) to amplification using primers which are flanking repeat pattern affected by a mutator phenotype or cold inter-Alu PCR followed by hybridization with a probe corresponding to an instability prone locus; d) subjecting the amplified fragments of step c) to electrophoretic fractionation on a polyacrylamide gel to determine the presence of a variation in band profile between tumor and tumor-free DNA indicating a genomic instability associated with a mutator phenotype; and e) employing means for comparing the allelic status of at least one instability prone locus in the DNA samples of step c).

5 Claims, 6 Drawing Sheets

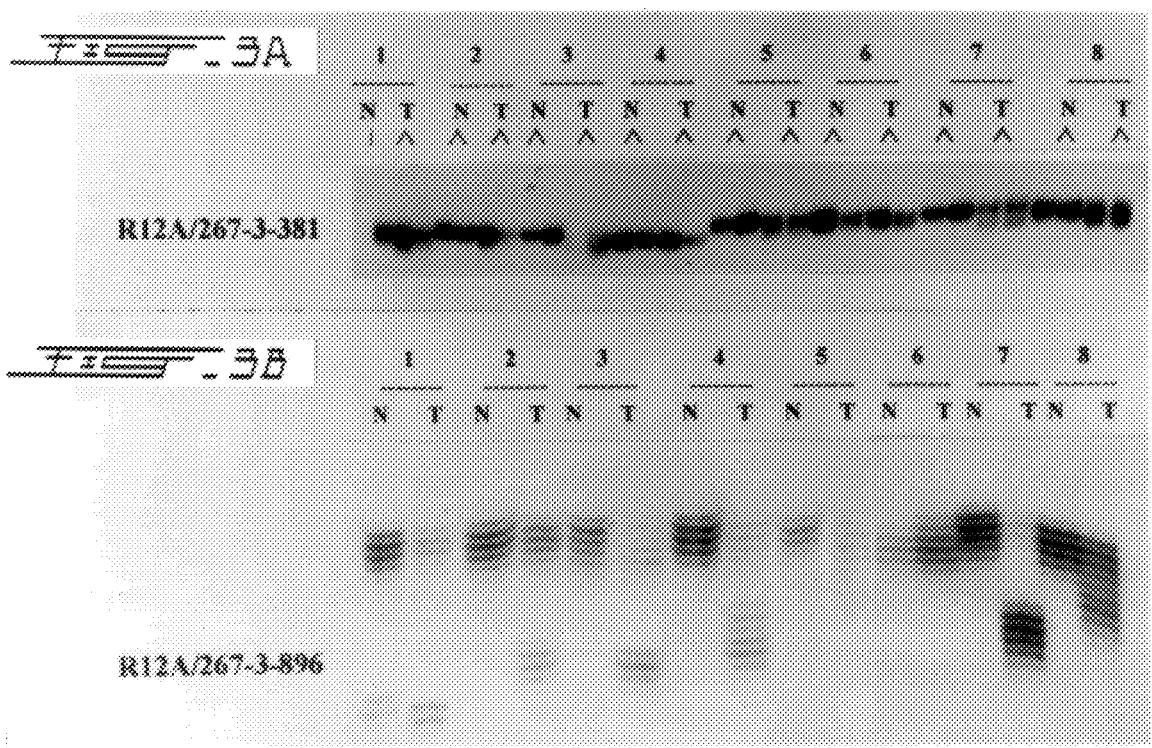

R12A/267-3-896

AGGCGAGACTCCGACTAAAAAAAAAAAAAAAAAANNGGCATTTATAAGATC
ATCTAAGTGATGACATCACAAGCACCTGTAATTGCTAACTCTGCTTTAAAGAAA
AACTCTAAACAGTTGGGCTTTACATCTGTTGCTAGTTTAATAACTGCAAAAGTCT
GCAGTTTTCAGAAAGGTGGGCCCTGATCCCCTTGTACGTGGTGTCCCTA
ATTTCAGACACGTAATAACAGGGTAAAGGTGTTGATGATATATGATTATAGCT
TATAGGGCTGCAGCCATTACTACAAGGAATCTCCATTCATTCGCTGTGT
GGCTGGCCCGNGAAATGACTTATCCACTCTGTACCTTCAGACCCACCTTTGT
AAGGAGGAATACCAACAGTCCCACAGAGTCTNNAGACTAAATAGGAT
GTCCTTTATGATTATAAATGACTTTCTGAGCTCCTGTACTATGCATATGGATG
GNAAGGACCCACGGGTTGACTGCGTGCCAGTGTCCAGGTGCTTCTCAAAG
GCAGCTTGAAGAAGACACGTGCCTAGAGGCGAAGTGTCCATTCACTCTG
TGAGGCTGGGGAATAGAATCGACAGAAAAGCCATTTAAAGCCATTCACTCTG
ACTTCTTAGAACAAACTGAAAGGAAACCCTTAACTTCCACGCCTAAGTAACA
AAAGGAGGAGGGGCTACTCTTTTGCAACCTTACCTTTTCTGCAGGGCAGAT
GGGAAATTGAAAGTACCTCTGAGTTGGTTTTGCTTTTGCAACAATCAGACGTT
TGCATAGGAGTGTAACTTGTAACTTCACTTCAGCCTCTGATGGGTTGCTGCCC
ACAACCAATCATACTGACTGGAGGCGGAGTCTCGCT

```
AGCGAGACTCCGTCTAAAAAAAAAAAAAAGTAATTATGCAAGCCTGTCTTC
TAGAGATAGACAGGCTTCCCGATAATCAGCTAAAAACACTTTGGGAGGCCGAG
GTGGACGGATCTCAGGAGTTCAAGACCAGCCTGGGCAACATGGCA
AGACGACCATCTCTACTAAAAATACAAAAATTCGGTGAGTGGTCGCGC
ATGCCAGTGTGCCCGGCTACTTGGGGACTGAGGCAGGAGGGTCGCTTGAGT
CTGAAGGTCGAGGTGTTCAGTGAGCTGTGTTCAAGGCGAGACCCTGTCTTAAA
AAAAAACCAAACAACAAAAATCAGTAAGCAAGTGAAAGAGGCTACTTCAAG
GAGGAAATAGGCAGGCAGGAACTGTGTTGTTCTACAAGAGAAAGGAGA
CTTCTAGAGCTATTCTCTTTAATATATGTGCATAAACAAGGAAAAGGAGA
AAAGAGGGTGGTGCCCTCACTCTGTCTTTGCTCCGTGAGAACAGTTGCATTC
CTACATGGAAAGCTCTTGGGAACCCGAGGGGCAGGGCAGATTGACTGGAG
TCCAACTTCAGAGCCGAGTCTCGCT
```

AGCGAGACTCCGTCAAAAAAAAAAAAAAAAAAAGCAATGGCTCTG
CTGTTACATAACGTTCAGCAGCACTGTAGGAATAAACACCTTTCCTGATGTCAG
AAGCTGCAGAAACGCTGCCAGTGCCTCCAGTGCAGAACTGGTCT
GGAAGGCTGCCATGTGTGCCCTGGAATCTTTTGGTGTTGG
ATTAATGGCATTCATGTTTCAGAAAACACCTCCAACCTAGTTAACAGGAAAAC
TGTTAGAGAATAAATAAAAACGGAGCGTTTAAAAGTTTTCCACTGAGAAGCAGT
TTGAAGAGTCAAGTCACCCTAGAGGAAAGCTGGGTATTTCTGTAGGTAGCCT
TGGAGGCTTTTGTGAACATGGCGTGCCACTGACAGGGTGGTTGGAGGAA
GGAAGAAAATGACCTGCGTGTTTACAAAATACATGCAGTCTTCCATGTGAAAGATTA
AGGACTTTCCCTGTTTTACAAAATACATGCAGTCTCTAATTAGAATC
TGGGATGAATGGTGGGTGGGGAGTCTCGCT

AGCGAGACTCCGCCTCAAAAAAAAAAAAAAGAAAAAGAAAAATCTCAGG
ACCACCCTAGAGTCCTTTGGTTACTCCTCCCACTGAACCAAGTCCATCCT
AAATATTCTCACATCTGCTGCTGCTGCAGTTCAGGCGGCCACA
TCCTGGCTCCCAGTAGGGCCACAGAGCACAGACTTACACACAGTCTCCT
GAGCCCAGGGTTCAGCACAGATGACATGACCCTTGTGTGCCACCAGATGT
CAACGCTGTCATTTCTGTTACCTGTGTGTGCCCCCACCTTTGGGTTGGAGGT
TCTAGAAAGGAGGGGGCTTATTTTTTACCCACCTAGCACTCTGCACACTTCAC
ACGGAGTCTCGCT

FIG-4D

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

A G C G A G A C T C    C G                                                                                        1 2

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

C A G A G C G A G A    C T C T                                                                                 1 4

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (iv) ANTI-SENSE: YES (xi) SEQUENCE DESCRIPTION: SEQ ID NO:3:

| CTGTTATTAA CGTGTCTG | 18 |
|---|---|

(2) INFORMATION FOR SEQ ID NO:4:

(i) SEQUENCE CHARACTERISTICS:
        (A) LENGTH: 889 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

| AGCGAGACTC | CGACTAAAAA | AAAAAAAAA | AAAAAAAGG | CATTTATAAG | ATCATCTAAG | 60 |
|---|---|---|---|---|---|---|
| TGATGACATC | ACAAGCACCT | GTAATTGCTA | ACTTCTGCTT | TAAAGAAAAA | CTCTAACAGT | 120 |
| TGGGCTTTAC | ATCTGTTGCT | AGTTTAATAA | CTGCAAAAGC | TCTGCAGTTT | TCTTCAGAAA | 180 |
| GGTGGGCCCT | GATCCCTTTT | GTACGTGGTG | TTCCCTAATT | TCAGACACGT | TAATAACAGG | 240 |
| GTAAAGGTGT | TGATGATATA | TGATTATAGC | TTATAGGGCT | GCAGCCATTT | ACTACACACA | 300 |
| AGGAATCTCC | ATTCATTCGC | TGTGTGGCTG | GCCCGGGAAA | ATGACTTATC | CACTCTGTAC | 360 |
| CTTCAGACCC | ACCTTTGTAA | AGGAGGAATA | CCAACAGTCC | CCTGCCACAG | AGTCTAGACT | 420 |
| AAATAGGATG | TCCTTTATGA | TTATGTTATA | AATGGACTGG | ACTCTAGCAT | GATTGAGCTA | 480 |
| GAAGGACCCA | CGGGTTGACT | TTTCTGAGCT | CCTGTACTAT | GCATAATGGA | TGGCAGCTTG | 540 |
| AAGAAGACAC | GTGCCTAGAG | CGAAGTGTCC | AGGTGCTTCT | CAAAGTGAGG | CTGGGGAATA | 600 |
| GAATCTGCAG | GCAGGGAATC | TAAAGCCATT | TCACTCTGAC | TTCTTAGAAC | CAAACTGAAA | 660 |
| GGAAACCCTT | AACTTTCCAC | GCCTAAGTAA | CAAAAGGAGG | AGGGGCTACT | CTTTTGCAAC | 720 |
| CCCTTACCTT | TTCTGCAGGG | CAGATGGGAA | ATTGAAAGTA | CCTCTGAGTG | GTTTTGCTTT | 780 |
| TTGCAACCAA | TCAGACGTTT | GCATAGGAGT | GTAACTTTGT | AACTTCACTT | CAGCCTCTGA | 840 |
| TGGGTTGCTG | CCCACAACCA | ATCATACTGA | CTGGAGGCGG | AGTCTCGCT | | 889 |

(2) INFORMATION FOR SEQ ID NO:5:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

| AGCGAGACTC | CGTCTAAAAA | AAAAAAAAA | AAGTAATTAT | GCAAGCCTGT | CTTCTAGAGA | 60 |
|---|---|---|---|---|---|---|
| TAGACAGGCT | TCCCGATAAT | CAGCTAAAAA | CACTTTGGGA | GGCCGAGGTG | GACGGATCTC | 120 |
| TTGAGCTCAG | GAGTTCAAGA | CCAGCCTGGG | CAACATGGCA | AGACGACCAT | CTCTACTAAA | 180 |
| AATACAAAAA | TAAATTCGCT | GGGAGTGGTC | GCGCATGCCA | GTGGTCCCGG | CTACTTGGGG | 240 |
| GACTGAGGCA | GGAGGGTCGC | TTGAGTCTGG | AAGGTCGAGG | CTGCAGTGAG | CTGTGTTCAA | 300 |

| AGCGAGACCC | TGTCTTAAAA | AAAACCAAAC | AACAAAAAAA | TCAGTAAGCA | AAGTGAAAGA | 360 |
| GGCTACTTCA | AGGAGGGAAA | TAGGGAGCAG | GGGCAGGAAC | TGCTGTTGTG | TTTCTACAAG | 420 |
| ACACCTTCTA | GAGCTATTCT | CTTTAATATA | TGTGCATAAA | ACACAAGGA | AAAGGAGAAA | 480 |
| AGAGGGTGGT | GGCCCTCACT | TCTGTCTTTG | CTCCGTGAGA | ACAGTTGCAT | TCCTACATGG | 540 |
| AAAGCTCTTG | GGGAACCCGA | GGGGCACGGG | CAGATTGACT | GGAGTCCAAC | TTCAGAGCCG | 600 |
| GAGTCTCGCT | | | | | | 610 |

(2) INFORMATION FOR SEQ ID NO:6:

(i) SEQUENCE CHARACTERISTICS:
(A) LENGTH: 567 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

| AGCGAGACTC | CGTCAAAAAA | AAAAAAAAA | AAAAAAAAA | AGCAATGGCT | CTGCTGTTAC | 60 |
| ATAACGTCAG | CAGCACTGTA | GGAATAACAC | CTTTTCCCTG | ATGTCAGAAG | CTGCAGAAAC | 120 |
| GCCTGCCAGT | GCAGAACGCT | CCTCCAGTGC | AAACTGGTCT | GGAAGGCTTG | GCCATGTGTG | 180 |
| CCCTGGAAAG | TTCTGGAATC | TTTTTGGTGT | TGGATTAATG | GCATTCATGT | TTCAGAAAAC | 240 |
| ACCTCCAAAC | CTAGTTAACA | GGAAAACTGT | TAGAGAATAA | ATAAACGGA | GCGTTTAAAA | 300 |
| AGTTTTCCAC | TGAGAAGCAG | TTTGAAGAGT | CAAGTCACCC | TAGAGGAAAG | CTGGGTATTT | 360 |
| TCTTGTAGGT | AGCCTTGGAG | GCTTTTGTGA | ACATGGCGGG | TGGTGGTTGA | CAGGGTGGTT | 420 |
| GGAGGAAGGA | AGAAAAATGA | CCTGCGTGCC | ACTCTTAATA | ATTGCCTCTT | AATTTAGAAT | 480 |
| CAGGACTTTT | CCCCCTGGTT | TTACAAAATA | CATGCAGTCT | TCCATGTGAA | AGATTATGGG | 540 |
| ATGAATGGTG | GGTGGCGGAG | TCTCGCT | | | | 567 |

(2) INFORMATION FOR SEQ ID NO:7:

(i) SEQUENCE CHARACTERISTICS:
(A) LENGTH: 390 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

| AGCGAGACTC | CGCCTCAAAA | AAAAAAAAA | AAAAAGAAA | AGAAAATCTC | AGGACCACCC | 60 |
| TAGAGTCCTT | TTGGGTTACT | CCTCCCACTG | AACCAAGTTC | CATCTCCTAA | ATATTCTCAC | 120 |
| ATCTTGCTGC | TGCTGCTGCT | GCAGCTTCAG | GCCGGGCCCA | CATCCTGGCT | CCCAAGTAGG | 180 |
| GCCCAGTTCC | CACGACAGCC | CCACTACGTC | TCTCCTGAGC | CCCAGGGTTC | AGCACAGATG | 240 |
| ACATGACTTA | CACAGCACAC | ACCAGATGTC | AACGCTGTCA | TTTCTGTTAC | CTGTGTGCCC | 300 |
| CTTCCCACCT | TTGGGTTGGA | GGTTCTAGAA | AGGAGGGGGG | CTTATTTTTT | ACCCACCTAG | 360 |
| CACTCTGCAC | ACTTCACACG | GAGTCTCGCT | | | | 390 |

DNA MARKERS TO DETECT CANCER CELLS EXPRESSING A MUTATOR PHENOTYPE AND METHOD OF DIAGNOSIS OF CANCER CELLS

BACKGROUND OF THE INVENTION (a) Field of the Invention

The invention relates to the use of inter-ALU PCR technique to examine the mutator phenotype in cancer cells, to detect and eventually map the affected genomic loci. More specifically, the invention relates to a method of diagnosis and/or prognosis of cancer cells.

(b) Description of Prior Art

In recent years, there has been significant progress in deciphering the molecular changes accompanying malignant transformation. A large number of tumors have been characterized as carrying a variety of chromosomal and submicroscopic genomic modifications, including activation of dominant-acting proto-oncogenes, inactivation of tumor suppressor genes and inactivation of metastasis suppressor genes. It is presumed that such tumors are descended from cell lineages that have accumulated a set of critical genetic lesions through random and relatively rare mutations at defined chromosomal locations. As an alternative tumor mechanism, some have postulated that a generalized, disseminated genomic instability, with attendant increased frequency of mutations at numerous unrelated loci, may represent a primary genetic mechanism in some tumors.

In a normal cell, multiple metabolic pathways control the overall accuracy of various functions, including DNA replication and repair, cell division and differentiation. A generalized genomic instability potentially could arise from disruption of one or more of these functions, including DNA replication, post-replicative proofreading, DNA repair, cell cycle check-point proteins, and DNA recombination. Mutations in genes that cause a generalized increase in the frequency of substitutions, insertions, deletions or other structural changes throughout the genome can be classified as "mutator" mutations.

Several clinical correlates have been cited in support of the theory that mutations in "mutator genes"may alter the regulation of a wide spectrum of genes, including those genes responsible for tumorigenesis. For example, individuals with the inherited disorder Xeroderma pigmentosum are defective in excision repair of DNA. A clinical correlate of this condition is a predisposition of these individuals to skin cancer following exposure to ultraviolet light.

In summary, malignant transformation may involve either of the following genetic pathways:

(1) accumulation in selected cell lineages of random but relatively infrequent mutations in proto-oncogenes, tumor suppressor genes and other genes directly related to tumorigenesis.

(2) mutation(s) in a mutator gene with resultant genomic instability.

There may be functional overlap in these two mechanisms in the sense that mechanism (2) may lead secondarily to mutations in known proto-oncogenes and tumor suppressor genes. However, the generalized and disseminated genomic instability of mechanism (2) may influence carcinogenesis through a wide array of known and unknown genetic mechanisms. As such, there may be little or no correlation between elevated levels of genomic instability and known mutational changes in characterized tumor-related genes. Moreover, it is conceivable that patients having tumors deriving from mechanism (2) may enjoy a relatively favorable prognosis compared to patients having tumors deriving from mechanism (1). This is due to the tendency of tumor cells having a generalized and disseminated genomic instability to continue to accumulate mutational changes, leading to cell disfunction and/or death. That is, these tumors may be relatively self-limiting in comparison to tumors deriving from mechanism (1). Moreover, individual having mutations in a mutator gene will be more susceptible to exposure to environmental factors leading to an increase of the mutational burden.

While a variety of nucleic acid probe-based assays are available to detect structural alterations in known tumor-related genes, there has been no reliable indicator of mechanisms involving generalized genomic instability in tumor formation. Nor has there been a reliable test to distinguish tumors arising from random mutations in tumor-related genes from those tumors arising from a more generalized genomic instability.

General genomic instability affecting a variety of microsatellite sequences was first observed in tumoral cells of the hereditary non polyposis colon cancer (HNPCC). This instability also known as mutator or replication error (RER) phenotype was shown to be symptomatic for the deficiency of cellular DNA mismatch-repair function indicating a novel genetic mechanism in tumorigenesis (Speicher, M. R., 1995, *Oncology Res.*, 7:267–275; Kolodner, R. D. et al., 1995, TIBS, 20:397–401). Several non HNPCC tumors, both sporadic and familial, were also found to be associated with the expansion/contraction of microsatellites but the pattern of instabilities differed (Speicher, M. R., 1995, *Oncology Res.*, 7:267–275). Since genetic instability is known to appear early in tumorigenesis and to persist afterwards examination of the RER phenotype has a potential predictive value for cancer initiation and progression.

International patent application published under No. WO 94/19492 on Sep. 1, 1994 discloses a method for the prognosis of cancer by analysis of tumor nucleic acids for evidence of genomic instability. More specifically, using a PCR-based approach, they revealed changes in the allelic pattern of microsatellite markers suggesting the presence of a mutator phenotype in colorectal patient. They used publicly available and commercial microsatellite markers with no apparent increased susceptibility to a RER phenotype. However, they found a positive correlation between colorectal cancer patients displaying a RER phenotype and a good prognosis. This is their main achievement, since they have not developed new markers.

In accordance with the invention, a series of markers that show an increased susceptibility to the presence of a mutator phenotype in HNPCC patients was developed. These markers are then more informative for the detection of tumors expressing a RER phenotype and therefore more adapted for that kind of analysis. The development of unstable tumor-specific markers will provide a very powerful tool capable of confirming the diagnosis (as well as early-detection) of a particular cancer type.

It would be highly desirable to be provided with a means to examine the mutator phenotype in cancer cells for the prognosis of patients, to detect and eventually map the affected genomic loci preferably affected by a mutator phenotype.

SUMMARY OF THE INVENTION

Inter-Alu PCR typing was used in both physical and genetic mapping (Sinnett, D. et al., *Genomics*, 7:331–334; Zietkiewicz, E. et al., 1992, *Proc. Natl. Acad. Sci. USA*, 89:8448–8451). Inter-repeat PCR simultaneously amplifies DNA fragments from multiple genomic loci where an increased density of simple sequence motifs is expected. In accordance with the present invention, two systems of inter-Alu PCR using primers, R12A/267 and R14B/264, directing amplification between Alu repeats in a tail-to-tail orientation were characterized in detail. Indeed polymorphisms due to length variability in the intervening amplified segments were relatively frequent and the majority of PCR products includes Alu poly-A tails.

In accordance with the present invention there is provided the application of inter-Alu PCR using the primers R12A/267 and R14B/264 to examine the mutator phenotype in HNPCC patients, to detect and eventually map the affected genomic loci.

More specifically, in accordance with the present invention there is provided a method of diagnosis or prognosis of tumor cells in a patient by detecting a mutator phenotype in the tumor which comprises the steps of:

a) obtaining a genomic DNA sample of the tumor;
b) obtaining a genomic DNA sample of a tumor-free tissue of the patient;
c) subjecting the DNA samples of steps a) and b) to amplification using primers which are flanking repeat pattern affected by a mutator phenotype or cold inter-Alu PCR followed by hybridization with a probe corresponding to an instability prone locus;
d) subjecting the amplified fragments of step c) to electrophoretic fractionation on a polyacrylamide gel to determine the presence of a variation in band profile between tumor and tumor-free DNA indicating a genomic instability associated with a mutator phenotype; and
e) employing means for comparing the allelic status of at least one instability prone locus in the DNA samples of step c).

The preferred tumor used in accordance with the present invention is a colorectal tumor.

In accordance with the present invention, the primers of step c) or d) are selected from the group consisting of R12A/267 (SEQ ID NO:1), R14B/264 (SEQ ID NO:2) and R12A/2671-896 (SEQ ID NO:31).

In accordance with the present invention, when PCR is used in step c) or d) of the method, the primers are R12A/267 (SEQ ID NO:1) and R12A/267-896 (SEQ ID NO:3).

In accordance with the present invention, when cold inter-Alu PCR is used in step d) of the method, the primers are R12A/267 (SEQ ID NO:1) and R14B/264 (SEQ ID NO:2) and the probe is selected from the group consisting of SEQ ID NO:4, SEQ ID NO:5, SEQ ID NO:6, SEQ ID NO:7 and hybridizing fragments thereof under stringency conditions.

In accordance with the present invention there is also provided a kit for diagnosis or prognosis of tumor cells in a patient by detecting a mutator phenotype in the tumor cells, which comprises:

a) R12A/267 (SEQ ID NO:1) and R12A/267-896 (SEQ ID NO:3) primers.

BRIEF DESCRIPTION OF THE DRAWINGS

FIG. 3 illustrates the analysis of the unstable loci, R12A/267-3-381 and R12A/267-3-896, by hybridization and locus-specific PCR, respectively; and FIGS. 4A–4D illustrate the complete DNA sequence of loci R12A/267-3-896 (SEQ ID NO:4), R12A/267-4-610 (SEQ ID NO:5), R12A/267-4-567 (SEQ ID NO:6) and R12A/267-3-381 (SEQ ID NO:7), respectively.

DETAILED DESCRIPTION OF THE INVENTION

Figure 1:
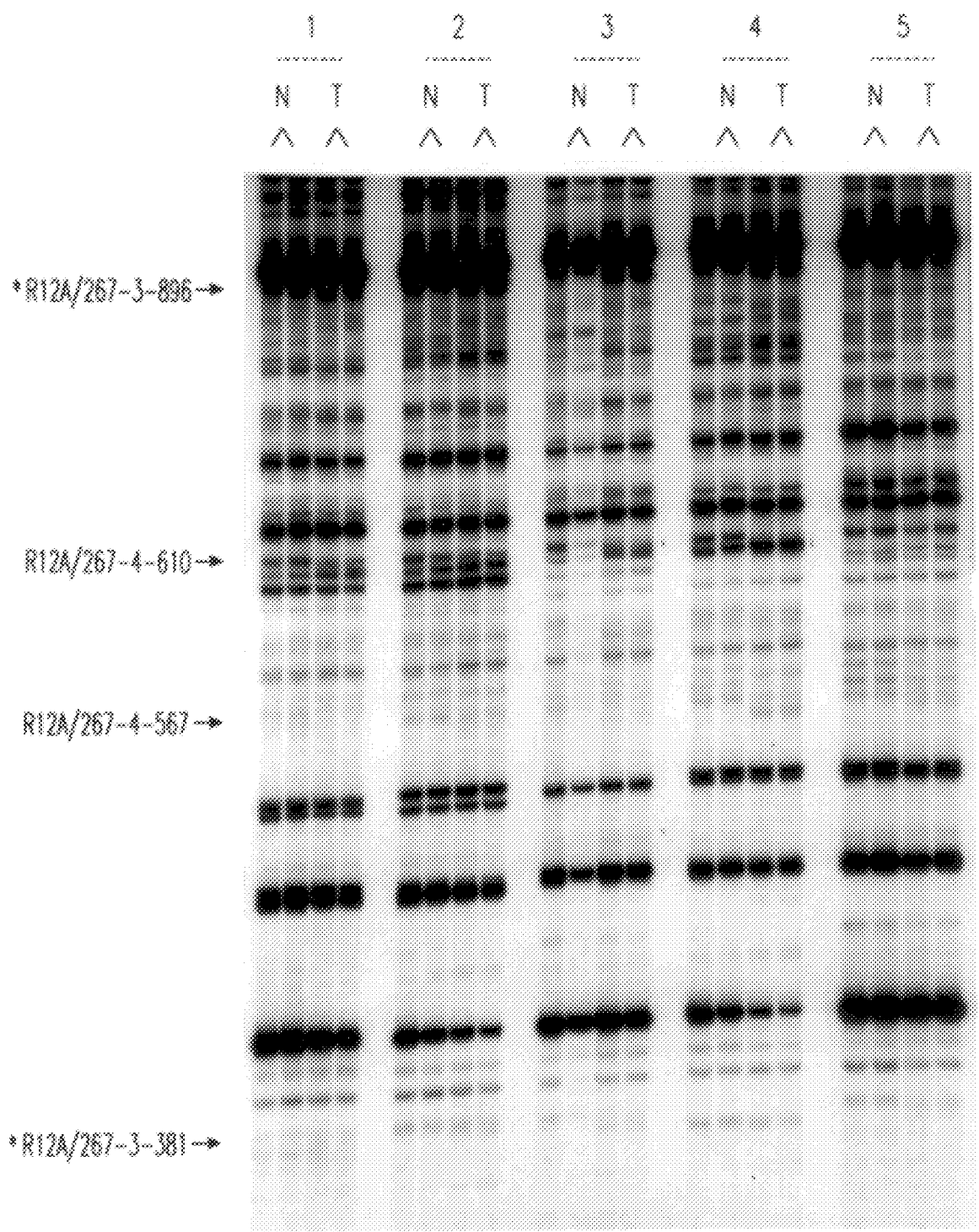
FIG. 1 is R12A/267 directed PCR amplification of matched pairs of normal (N) and tumoral (T) DNA samples from HNPCC patients.

A mutator phenotype due to a DNA mismatch-repair deficiency is usually detected through typing a number of microsatellite markers. Here, eight hereditary non polyposis colon cancer (HNPCC) patients with microsatellite instability were investigated by inter-Alu PCR, known to amplify DNA segments that represent preferential targets of replication errors. Among 40 to 60 PCR bands revealed in a single PCR experiment, more than 20% were found altered when matched pairs of normal and tumoral samples were compared. Gain or loss of bands were rare, whereas shifts and changes in signal intensity accounted for most of the alterations. Certain bands were seen affected only once, while the instability in others were common.

These results suggest that some regions are more susceptible than others to the expression of a mutator phenotype. Four such bands seen altered in more than 4 patients, were further characterized and shown to be unstable due to contractions of the Alu poly-A tails. Interestingly, none of the bands representing loci previously shown to be polymorphic in the population was observed unstable.

The inter-Alu PCR technique of the present invention appears to be a robust, cost-effective and sensitive technique to reveal the mutator phenotype in cancer cells.

DNA samples

Tumoral and normal DNA samples from 8 HNPCC patients known to display a mutator phenotype were kindly given by M. Perucho (California Institute of Biological Research) and D. J. Tester (Mayo Clinic).

Inter-Alu PCR

Alu specific primers (used one at a time): R12A/267, AGCGAGACTCCG (SEQ ID NO:1), and R14B/264, CAGAGCGAGACTCT (SEQ ID NO:2), span 12 and 14 nucleotides of the Alu consensus sequence downstream from position 267 and 264, respectively. The primer name starts with a letter R, which denotes a primer identical to the Alu coding strand, thus directing amplification downstream (to the right) of a genomic Alu template. The two following digits define the length of the oligonucleotide (12 for dodecanucleotide). The letter A in R12A/267 denotes the identity whereas the letter B in R14B/264 indicates a non-perfect match with the consensus, due to a C to T substitution at the 3' end of the primer. The reactions (total volume of 20 $\mu$l) were performed in 10 mM Tris-HCl (pH 8.8, determined at 25° C.), 50 mM KCl, 1.5 mM $MgCl_2$, 2 $\mu$Ci [$\alpha$-32p] dCTP (3000 Ci/mmol, NEN-Dupont), 100 $\mu$M dNTP each and 1 $\mu$M of one primer, using 5–10 ng of DNA template (or 50 ng sample from somatic cell hybrids, BIOS). After denaturation, at 94° C. for 7 min, 1 unit of Taq DNA polymerase (BRL) was added at 80° C., followed by 27 amplification cycles (30 sec at 94° C., 45 sec at 50° C. and 120 sec at 72° C.) and an extension at 72° C. for 7 min. The PCR reactions were performed in a DNA thermal cycler (Perkin/Elmer/Cetus). Each sample was amplified in duplicate and the PCR products were run in parallel in adjacent lanes during electrophoresis.

Polyacrylamide gel electrophoresis

About one-fifth of the PCR products was loaded onto a 6–8% polyacrylamide gel (acrylamide: N,N'-methylenebisacrylamide ratio of 29:1) cast in a 0.04 cm width sequencing cell. Electrophoresis was carried out in 1×TBE buffer (90 mM Tris-borate, pH 8.3, 2 mM EDTA) at room temperature. Gels were dried and exposed at −80° C. with an intensifying screen up to 2 days.

Cloning and sequencing

The bands of interest were excised from the dried gel, eluted by incubation in 1 mM EDTA/0.5M ammonium acetate/0.1% SDS, pH 8, for 18 h at 37° C. and ethanol precipitated. The eluted DNA fragment served as a template for a second PCR amplification (conditions as described above, except that no genomic DNA was present). The amplification product was purified by agarose gel electrophoresis and cloned in pBluescript™ II KS+ (Stratagene). DNA preparations from 4–6 positive clones were used for sequence determination with the ABI 373 A DNA™ sequencer.

Analysis of selected loci.

For Southern blots, non-radioactive inter-Alu PCR products were transferred onto Hybond™ N+ membrane (Amersham) and hybridized with cloned locus-specific DNA fragments (locus R12A/267-4-610, R12A/267-4-567 and R12A/267-3-381). The oligonucleotide CTGTTAT-TAACGTGTCTG (SEQ ID NO:3) (located downstream of the unstable Alu poly-A tail in locus R12A/267-3-896) was radioactively labeled, and used together with the oligonucleotide R12A/267 for locus-specific amplification; the product was subsequently analyzed on a 6% denaturing polyacrylamide gel.

Statistical analysis

Under null hypothesis the band shifts in the tumoral samples from the eight patients analyzed occur randomly. The deviation of the data from the expected binomial distribution was tested by chi-square statistics.

Results

We analyzed matched tumoral and normal DNAs from 8 unrelated HNPCC patients with microsatellite instability. Two different Alu-specific primers, R12A/267 and R14B/264, both anchored near the 3'-end of Alu sequences, directed PCR amplification between Alu repeats in a tail-to-tail orientation. A typical Alu-PCR "fingerprint" obtained with R12A/267 primer is shown in FIG. 1. Arrows indicate "unstable" loci characterized in Table 2. Two of them, indicated by the asterix, are presented on FIG. 3. Upper part of the Figure with locus R12A/267-3-869, corresponds to the shorter exposure time of the same gel. Amplification products were analyzed within the size range 0.3 to 1.5 kb. Each PCR reaction revealed 40 to 60 anonymous bands originating from a variety of genomic loci. Because of the multiple-locus character of this amplification, each DNA sample was amplified in duplicate. Bands present in both normal and tumoral genomes of the same patient but different between individuals, represent polymorphisms, while differences between banding pattern of normal and tumoral cells DNA from the same patient suggest somatic mutations.

Each patient contains several loci that were altered in tumoral DNA. These alterations can be seen as shifts, or losses of bands, as well as changes in signal intensity. Their respective frequencies estimated from the total number of analyzable bands are provided in Table 1.

TABLE 1

Frequency and type of genomic bands altered in HNPCC patients revealed by inter-Alu PCR using primers R12A/267 and R14B/264

| Primer | Patient | Number of bands | | | | | |
|---|---|---|---|---|---|---|---|
| | | Intensity | Shift | Altered Loss | Gain | Sum | Analysable |
| R12A/267 | 1 | 4 | 8 | | | 12 | 50 |
| | 2 | 3 | 7 | 1 | | 11 | 49 |
| | 3 | 1 | 10 | | 3 | 14 | 42 |
| | 4 | 2 | 8 | 1 | 1 | 12 | 43 |
| | 5 | 4 | 3 | | | 7 | 42 |
| | 6 | 2 | 5 | | | 7 | 40 |
| | 7 | 2 | 4 | | | 6 | 40 |
| | 8 | 2 | 8 | 1 | 1 | 12 | 48 |
| | Average #(%) | 2.5 (5.6) | 6.6 (15) | 1 (0.8) | 1.6 (1.4) | 10 (23) | 44 |
| R14B/264 | 1 | 4 | 8 | | 1 | 13 | 62 |
| | 2 | 5 | 12 | | 3 | 20 | 65 |
| | 3 | 1 | 17 | 1 | 3 | 22 | 66 |
| | 4 | 1 | 15 | 1 | 1 | 18 | 56 |
| | 5 | 2 | 11 | 1 | 1 | 15 | 61 |
| | 6 | 1 | 4 | 1 | 1 | 7 | 31 |
| | 7 | 2 | 5 | | 2 | 9 | 32 |
| | 8 | 4 | 5 | | 1 | 10 | 35 |
| | Average #(%) | 2.5 (5.2) | 9.6 (18) | 1 (1) | 1.7 (3.3) | 14 (28) | 53 |

On average, 23% and 28% of the bands were seen altered when using R12A/267 and R14B/264 Alu-PCR system, respectively. A similar ratio between different categories of alterations was observed in both cases. The less frequent changes accounting for 1–3% of all amplified products were either the loss or gain of a band. The changes in signal intensity were detected in 5%, while the most frequently observed alterations were variations in electrophoretic mobility (shift) seen in 15–18% of the bands. Interestingly, certain bands appeared to be altered in several patients suggesting that these events were not random. In the R14B/264 system, out of the 19 bands that were altered more than once, seven were seen affected in at least 4 out of the 8 HNPCC patients investigated. For the R12A/267 system, these numbers were 15 and 5, respectively. With 7 bands seen shifted only once this sums up to 22 bands out of the 44 analysable.

Figure 2:
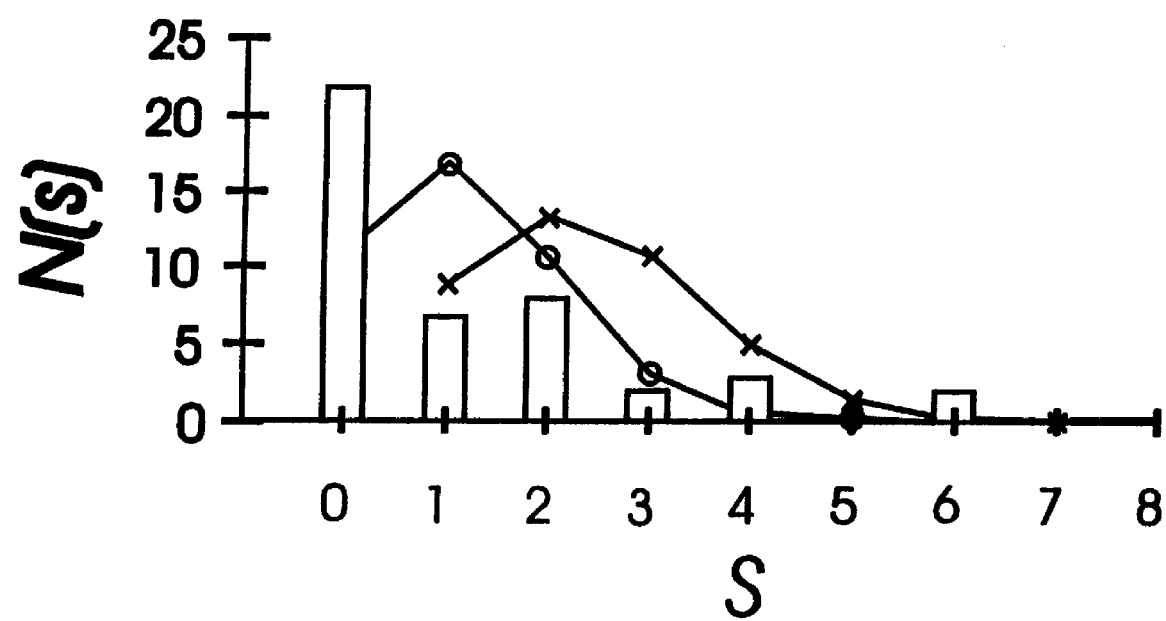
FIG. 2 illustrates the distribution of the band shifts revealed by R12A/267 Alu-PCR.

As seen in FIG. 2 these shifted bands are not randomly distributed assuming either (i) that all analysable bands are equally likely to undergo shifts, or more conservatively, (ii) that only those seen affected at least once (i.e. susceptible to RER) are considered ($p<0.001$ and 0.005, respectively). N(s) is the number of bands with S (0, 1, 2, . . . , 8) shifts (FIG. 2). Columns represent the observed numbers, whereas lines with circles and crosses correspond to model I and II (as explained in Results) of expected distribution, respectively.

Significant deviation from expected value was also seen under both assumptions from R14B/264 system ($p<0.001$). This confirms the conclusion that some bands are preferentially affected by RER in HNPCC cells.

To identify the molecular nature of instabilities in these bands, 4 of them which are indicated in FIG. 1 were further characterized. Arrows indicate "unstable" loci characterized in Table 2.

bands from five R12A/267 loci known to exhibit length variability was found unstable in the 8 patients studied suggesting that length polymorphism in the population and sensibility to the RER are not necessarily inter-connected.

The phenomenon of genomic instability play an important role in the development of malignancies where an increased rate of replication errors makes the alterations of critical cancer genes more probable. This phenomenon was usually studied by typing a number of polymorphic microsatellites used otherwise as tools in linkage mapping studies (Speicher, M. R., 1995, *Oncology Res.*, 7:267–275). Although such instable loci are also revealed by inter-Alu PCR, this technique represents more general and less biased approach since it targets a variety of genomic fragments with a potential to reveal RER. Compared to other approaches, inter-Alu PCR is more robust because it appears to target sequence repeats that are especially sensitive to RER.

The comparison of matched normal-tumoral DNAs from 8 unrelated HNPCC patients allowed us to observe alterations in more than 20% of analysable bands. These were

TABLE 2

Characterization of loci most sensitive to instability

| Locus Name | DNA Source | Chromosomal Localization | Unstable sequences |
|---|---|---|---|
| R12A/267-3-896 | N | 16 | AGCGAGACTCCGACTAAAAAAAAAAAAAAAAAAAAAAAAAGGCATTTAT. . . |
| (SEQ ID NO:4) | T | | AGCGAGACTCCGACTAAAAAAAAAAAAAA  *  GGCATTTAT. . . |
| R12A/267-4-610 | N | 2 | AGCGAGACTCCGTCTAAAAAAAAAAAAAAAAAAGTAATTATGCAAG. . . |
| (SEQ ID NO:5) | T | | AGCGAGACTCCGTCTAAAAAAAAAAAAAA  *  GTAATTATGCAAG. . . |
| R12A/267-4-567 | N | 6 | AGCGAGACTCCGTCAAAAAAAAAAAAAAAAAAAAAAAAAAGCAAT. . . |
| (SEQ ID NO:6) | T | | AGCGAGACTCCGTCAAAAAAAAAAAAAAAAAAAAAAA  *  GCAAT. . . |
| R12A/267-3-381 | N | 7 | AGCGAGACTCCGCCTCAAAAAAAAAAAAAAAAAAAAGAAAAGAAAAT. . . |
| (SEQ ID NO:7) | T | | AGCGAGACTCCGCCTCAAAAAAAAAAAAAA  *  GAAAAGAAAAT. . . |

The presence of genomic instability and the identity of unstable bands was confirmed by locus-specific amplification in the case of R12A/267-896 and by hybridization using the corresponding cloned DNA fragments as probes in the remaining three loci (FIG. 3).

Analysis of the unstable loci is as follows.

A) Southern analysis of the R12A/267-PCR products using radioactively labeled probe for locus R12A/267-3-381.

B) Amplification products using radioactively labeled R12A/267-3-869 specific primer (N, normal DNA; T, tumoral DNA samples.

These two loci are indicated by asterix in FIG. 1.

Loci R12A/267-4-567, R12A/267-3-381, R12A/267-3-896 and R12A/267-4-610 were found unstable in 5,6,7 and 8 HNPCC patients, respectively. The corresponding probes were also used for hybridization to the PCR-amplified DNA derived from human-hamster somatic hybrid cell lines leading to their chromosomal assignment: no clustering of chromosomal locations was observed (Table 2).

The sequencing of the cloned unstable DNA segments as well as their counterparts from normal cells revealed that shifts in every analyzed band was caused by deletions in the poly-A tail of Alu elements (Table 2). The number of A-residues involved in the deletions were between 3 and 9 obtained from sequencing of several clones differing in the number of A-residues in the affected region.

Since a number of polymorphisms revealed by R12A/267 system were earlier characterized, the relationship between a site polymorphic in the population and its instability in RER+ cancer cells was investigated. None of the allelic subdivided in four major types of alterations. Decreased signal of a band presumably reflects an allelic loss, whereas a signal increase or appearance of a new band may represent aneuploidy or amplification. Similar quantitative effects in inter-repeat PCR of normal and malignant DNA samples were also reported by Peinado et al. (Peinado, M. A. et al., 1992, *Proc. Natl. Acad. Sci. USA*, 89:10065–10069). The less frequently observed alterations were disappearances of bands previously shown to be due to loss of heterozygosity (LOH). The most common were changes in electrophoretic mobility that are typically associated with a mutator phenotype. Such relative proportions of the observed alterations could be expected assuming that genomic instability, unlike LOH, appears earlier in tumor development and is not associated with gross chromosomal abnormalities. All instabilities which we have characterized were due to deletions in poly-A tails of Alu elements suggesting that certain sequence repeats are more sensitive to the expression of RER phenotype. These findings suggest a more penetrant mechanism for generation of instabilities at (A)n than at (CA)n repeats. Therefore inter Alu PCR could be extremely useful in studying pattern of genetic instabilities in sporadic cancer assuming that mutation in different repair genes or even unknown ones could result in different patterns of alteration. The frequency of unstable loci due to shift in electrophoretic mobility was 15–18%. Assuming that most of these shifts occur in Alu-tails present in 80% of about $6 \times 10^5$ copies of these repeats in the human genome, one expects near $10^5$ to be affected by RER all over. Most Alu repeats are dispersed in non-coding sequences, therefore great majority of these mutations are presumably not deleterious. One expect loci that belong to the same repeat motif (or pattern) to be equally likely sensitive to the expression of RER phenotype. The present results showed that some of them are preferentially affected by RER. This preferential occurrence of replication errors at certain loci may be due to its sequence context, chromatin organization or its status with respect to replication. It remains to be shown whether or not some loci can be altered in a tissue-specific manner, thus generating tumor-dependent pattern of alteration.

Diagnosis of the disease and the prognosis for the treatment may be tightly linked to the presence of a mutator phenotype, particularly to the loci preferentially affected by RER, thus opening a possibility of developing test with important predictive value.

In accordance with the present invention, there is demonstrated the usefulness of inter-Alu PCR to identify and isolate genomic loci sensitive to RER. Compared with genomic screening using single copy DNA markers, simultaneous analysis of DNA variation at multiple loci is efficient and greatly increases the informativity of the system. It remains to be explored to what extent the pattern of genetic instability revealed by inter-Alu PCR will be characteristic and thus diagnostic for a given type of cancer cells.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of detecting a mutator phenotype of tumor cells in a patient, which comprises the steps of:
   a) obtaining a genomic DNA sample of said tumor;
   b) obtaining a genomic DNA sample of a tumor-free tissue of said patient;
   c) subjecting the DNA samples of steps a) and b) to amplification using primers which are flanking a repeat pattern characteristic of a mutator phenotype or subjecting the DNA samples of steps a) and b) to non-radioactive inter-Alu PCR, wherein the primers employed are specific single sequence primer R12A/267-896 (SEQ ID NO.:3) and a primer selected from the group of Alu primers consisting of R12A/267 (SEQ ID NO:1) and R14B/264 (SEQ ID NO:2);
   d) subjecting the amplified fragments of step c) to electrophoretic fractionation on a polyacrylamide gel followed by hybridization with a probe corresponding to at least one instability prone locus; and
   e) comparing the hybridization results of said instability prone locus of fractionated tumor DNA and tumor free DNA of step c) to determine the presence of a variation in band profile, thereby detecting genomic instability associated with a mutator phenotype.

2. A method of detecting a mutator phenotype of tumor cells in a patient, which comprises the steps of:
   a) obtaining a genomic DNA sample of said tumor;
   b) obtaining a genomic DNA sample of a tumor-free tissue of said patient;
   c) subjecting the DNA samples of steps a) and b) to non-radioactive inter-Alu PCR, wherein non-radioactive inter-Alu PCR is performed using either R12A/267 primer (SEQ ID NO:1) or R14B/264 primer (SEQ ID NO:2);
   d) subjecting the amplified fragments of step c) to electrophoretic fractionation on a polyacrylamide gel followed by hybridization with a probe corresponding to at least one instability prone locus; and
   e) comparing the hybridization results of said instability prone locus of fractionated tumor DNA and tumor free DNA of step c) to determine the presence of a variation in band profile, thereby detecting genomic instability associated with a mutator phenotype.

3. The method of claim 2, wherein said probe corresponding to an instability prone locus is selected from the group consisting of SEQ ID NO:4, SEQ ID NO:5, SEQ ID NO:6, SEQ ID NO:7 and fragments thereof; wherein said fragments specifically hybridize to amplified fragments of step d) with the same specificity as probe SEQ ID NO:4, SEQ ID NO:5, SEQ ID NO:6 or SEQ ID NO:7.

4. The method of claim 1, wherein the tumor is a colorectal tumor.

5. The method of claim 1, wherein the PCR primers are Alu primer R12A/267 (SEQ ID NO:1) and specific single sequence primer R12A/267-896 (SEQ ID NO:3).

* * * * *